Figure 1:
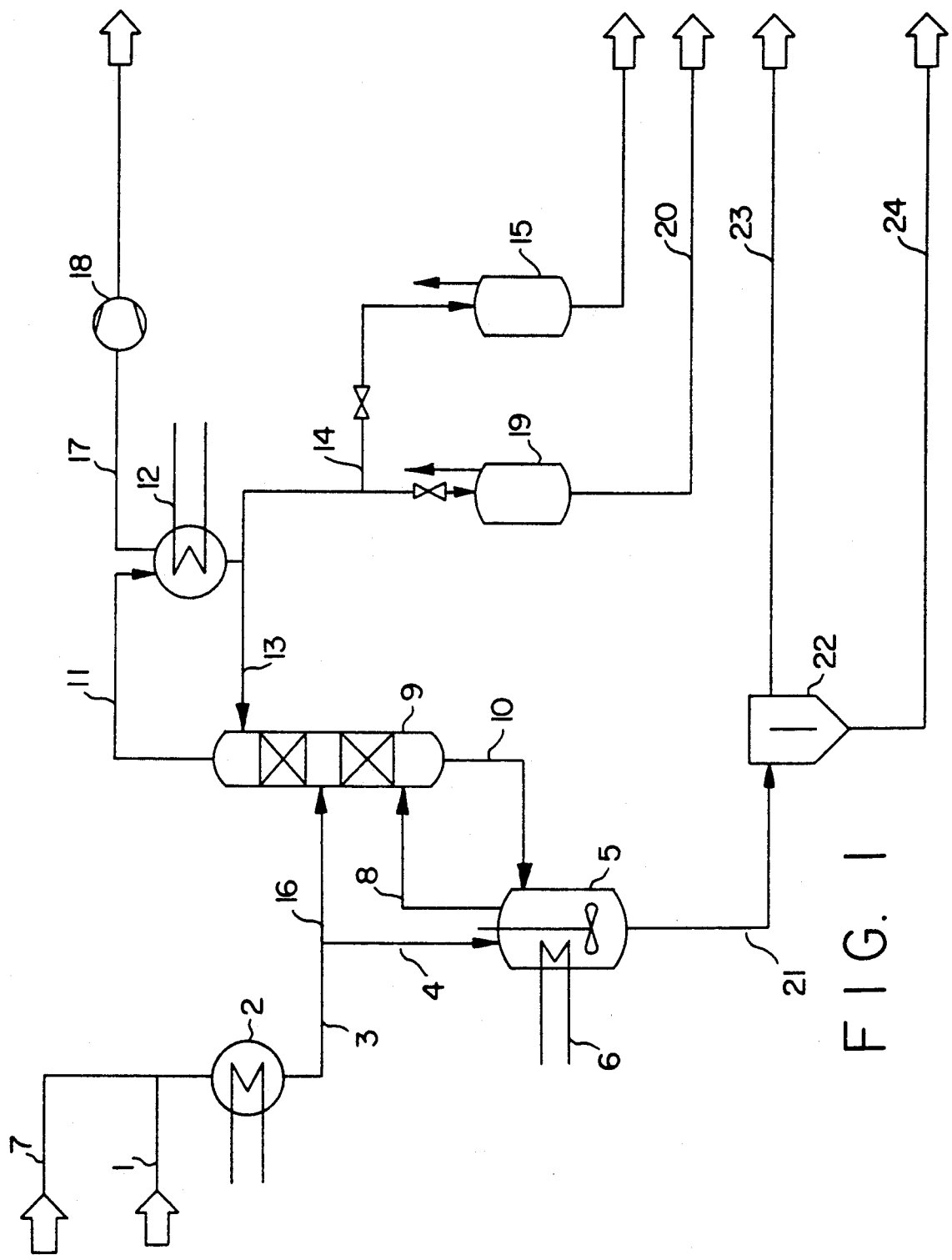

United States Patent [19]

Peukert et al.

[11] Patent Number: 5,254,722
[45] Date of Patent: Oct. 19, 1993

[54] PROCESS FOR THE PRODUCTION OF TRIGLYCERIDES

[75] Inventors: Eberhard Peukert, Hilden; Horst Rutzen, Langenfeld; Gerhard Wollmann, Hilden, all of Fed. Rep. of Germany

[73] Assignee: Henkel Kommanditgesellschaft auf Aktien, Duesseldorf, Fed. Rep. of Germany

[21] Appl. No.: 195,995

[22] Filed: May 19, 1988

[30] Foreign Application Priority Data

May 20, 1987 [DE] Fed. Rep. of Germany ....... 3716950

[51] Int. Cl.$^5$ .................. C07C 67/03; C07C 69/18
[52] U.S. Cl. ..................... 554/227; 560/204; 560/234
[58] Field of Search ............ 260/410.7, 410.6; 560/234, 204

[56] References Cited

U.S. PATENT DOCUMENTS 4,747,969 5/1988 Rupllius et al. ................. 260/415

FOREIGN PATENT DOCUMENTS 0150794 8/1985 European Pat. Off. .
802261 2/1981 U.S.S.R. .......................... 260/410.7

OTHER PUBLICATIONS

Nobile et al., CH-A-422, vol. 61, col. 1931, (1963).

Primary Examiner—Arthur C. Prescott
Attorney, Agent, or Firm—Ernest G. Szoke; Wayne C. Jaeschke; Daniel S. Ortiz

[57] ABSTRACT

A process for the production of triglycerides of $C_1-C_4$ alkyl esters of $C_6-C_{22}$ fatty acids:

a) where dry sodium carbonate catalyst is dissolved in glycerol and mixed with a molar excess of preferably the methyl ester of $C_6-C_{22}$ fatty acid at a temperature between about 150° C. and 250° C. at less than atmospheric pressure and under substantially anhydrous conditions to produce an initial reaction mixture containing the corresponding triglycerides of said fatty acids, and partially reacted glycerol with unreacted hydroxyl groups (OH values 10–40), b) thereafter, a portion of the initial reaction mixture is reacted with additional $C_1-C_4$ alkyl ester of $C_6-C_{22}$ fatty acid under conditions to achieve substantially full conversion of said unreacted hydroxyl groups (OH values of 5 or less), and c) a product containing the corresponding triglycerides of said fatty acids is separated from unreacted alkyl ester and from the sodium carbonate catalyst. Improved light colored triglyceride products are achieved and can be separated readily from the sodium carbonate catalyst by filtration.

21 Claims, 2 Drawing Sheets

PROCESS FOR THE PRODUCTION OF TRIGLYCERIDES

BACKGROUND OF THE INVENTION

1. Field of the Invention

This invention relates to a process for the production of triglycerides of $C_6$–$C_{22}$ fatty acids.

2. Statement of Related Art

In the production of methyl esters by reaction of oils, particularly coconut oil or palm kernel oil, large quantities of so-called first-cut methyl esters, i.e. $C_8$–$C_{12}$ methyl esters, are inevitably formed due to the nature of the starting material. The quantity in which these first-cut methyl esters are formed is generally greater than the demand, so that there is considerable interest in a process for the production of triglycerides from the corresponding short-chain methyl ester mixtures directly, i.e. without preliminary conversion of the methyl esters into the corresponding fatty acids.

Processes for the production of triglycerides of the type mentioned above are known in which sodium methylate and sodium hydroxide are used as alkaline catalysts. However, the triglycerides obtained are dark in color and require elaborate purification for use in the food industry. In addition, the reaction systems show a tendency towards emulsification, in addition to which the sodium salts of the fatty acids formed as secondary products are difficult to remove.

DESCRIPTION OF THE INVENTION

Other than in the operating examples, or where otherwise indicated, all numbers expressing quantities of ingredients or reaction conditions used herein are to be understood as modified in all instances by the term "about".

The present invention is directed to a process for the production of triglycerides of $C_6$–$C_{22}$ fatty acids, and more particularly triglycerides of $C_6$–$C_{12}$ fatty acids by the reaction of $C_1$–$C_4$ alkyl esters of the fatty acids with glycerol in the presence of an alkali metal carbonate catalyst and glycerol.

The triglycerides produced in accordance with this invention include light colored products which are especially useful. These products have a wide range of commercial applications. Triglycerides derived from short-chain ($C_6$–$C_{12}$) fatty acids are marketed, for example, under the name Delios ®. The products are used as components of aromas and essences, for the surface treatment of dried fruits and tacky candy goods, and as base oils for the production of release agents for the confectionary field, and the like.

More specifically, one embodiment of the process according to this invention comprises the following steps and conditions:

a) A mixture of dry alkali metal carbonate, preferably sodium, potassium or lithium carbonates, and glycerol is added to dried fatty acid alkyl esters as described above which are heated to a temperature of 150° C. to 250° C. in a quantity corresponding to a molar ratio of glycerol to the fatty acid alkyl ester of preferably between 0.15:1 to 0.30:1 and at such a rate that the glycerol preferably remains soluble in the reaction mixture. A slight excedence of solubility, e.g., up to 10% is also acceptable. The term substantially soluble is employed herein to characterize these conditions.

b) After addition of the glycerol, more fatty acid alkyl ester is added to the boiling reaction mixture in a quantity preferably of at least 10%, based on the fatty acid alkyl ester used in step a), to react any unreacted hydroxyl groups of the glycerol.

c) The entire reaction is carried out under a light vacuum, i.e., less than atmospheric pressure, and $C_1$–$C_4$ alcohols formed are continuously distilled off.

d) The fatty acid alkyl ester is removed by distillation from the reaction mixture obtained which consists predominantly of fatty acid triglyceride, fatty acid alkyl ester and sodium carbonate.

e) Sodium carbonate is separated off and, f) Fatty acid triglyceride is purified by conventional methods.

The molecular weight of the $C_9$ fatty acid alkyl ester is preferably used as the basis for calculating the molecular weight of the fatty acid alkyl esters present in the form of a mixture. The addition of the fatty acid alkyl ester in step b) is also made to reduce the boiling point of the glyceride/fatty acid alkyl ester mixture.

It is essential to use substantially anhydrous reactants and catalysts which include carefully dried fatty acid alkyl esters, glycerol and sodium carbonate. Water contents of 1% by weight in the reaction mixture cause the undesireable formation of soaps or emulsions. Water contents of less than 1% and preferably less than 0.5% and most preferably less than 0.1% are employed in this invention.

The methyl ester is preferably used as the fatty acid alkyl ester.

In one advantageous embodiment of the invention, since the $C_1$–$C_4$ alcohol which is distilled off always contains appreciable fatty acid alkyl ester, this mixture is rectified and the fatty acid alkyl ester thus obtained is returned to the reaction mixture.

In another advantageous embodiment, it is also possible to introduce the mixture of dry sodium carbonate in glycerol directly into the rectification column during the reaction. A reaction to produce triglycerides takes place in the rectification column itself. The triglycerides thus formed are returned to the actual reaction mixture together with unreacted fatty acid alkyl ester.

In another advantageous embodiment of the invention, the process is carried out continuously. This embodiment of the process comprises the following steps and conditions:

a) A multi-plate, heatable reaction zone in communication and preferably surmounted by a rectification zone is employed for the reaction process. The term multi-plate is understood to include conventional column packing materials as well as physical distillation trays as are well known in the art.

b) The glycerol/sodium carbonate solution is introduced into the upper part of the reaction column preferably after heating it to the reaction temperature.

c) The fatty acid alkyl ester is introduced into the middle part of the reaction column. The ester is optionally introduced in the form of superheated vapor.

d) More fatty acid alkyl ester, also optionally as superheated vapor, is introduced below the point at which the fatty acid alkyl ester is fed into the reaction column in order to react any unreacted glycerol.

e) $C_1$–$C_4$ alcohol and fatty acid alkyl ester are separated in the rectification column and the $C_1$–$C_4$ alcohol is distilled off overhead.

f) Triglyceride/fatty acid alkyl ester/sodium carbonate mixture is removed from the sump of the reaction column. Fatty acid alkyl ester is evaporated in a suitable zone such as the sump evaporator and preferably returned at least partly to the column as vapor phase above the sump. The fatty acid triglyceride produced is separated from sodium carbonate and purified by conventional methods.

The invention is desribed in more detail with reference to the accompanying drawings.

FIG. 1 diagrammatically illustrates an installation for carrying out the process according to the invention in non-continuous or batch fashion.

Figure 2:
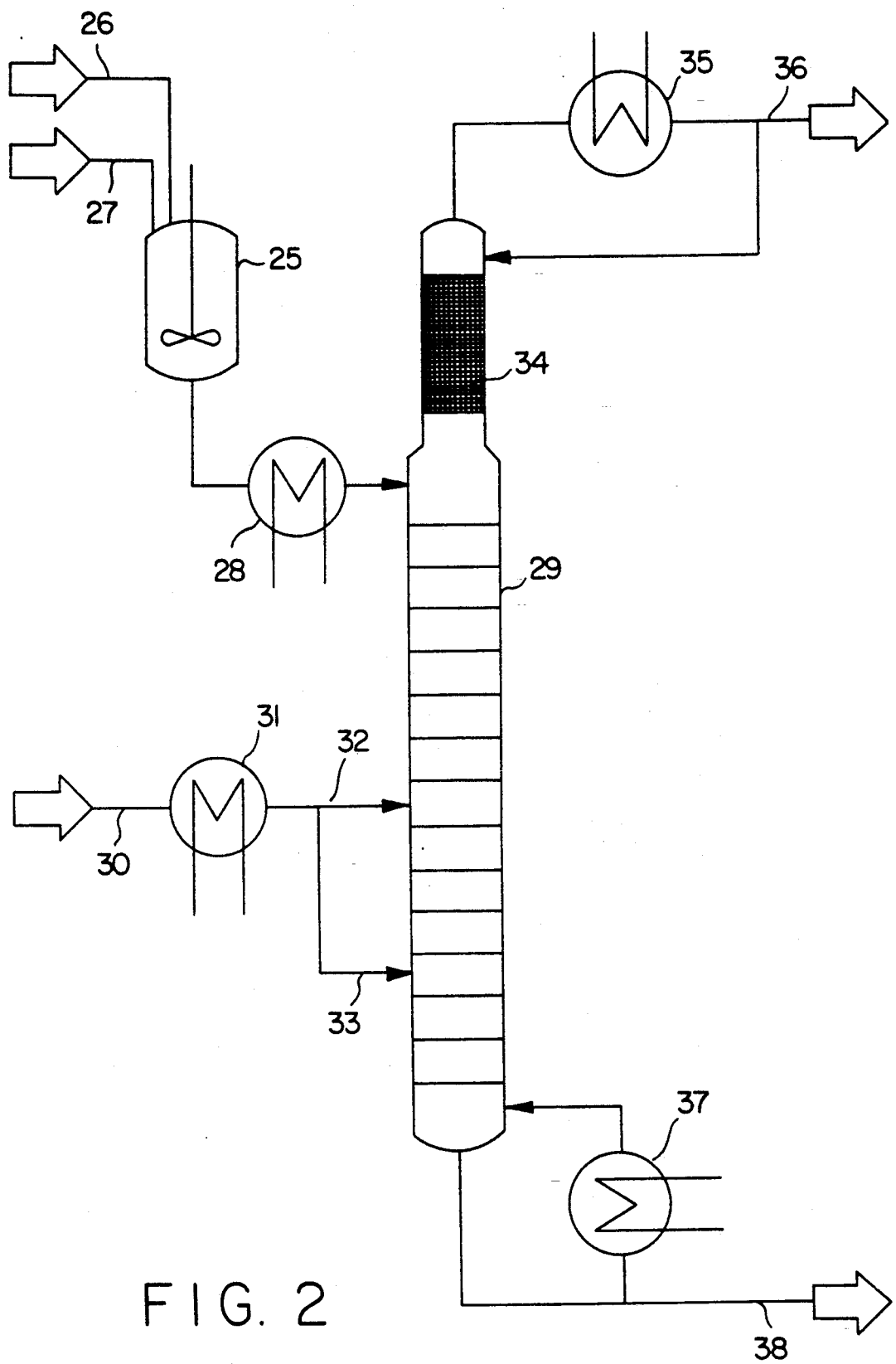

FIG. 2 diagrammatically illustrates the reactor portion of a process for continuously carrying out the present invention.

In the installation shown in FIG. 1, the fatty acid alkyl esters as described above are fed through a pipe I to a heat exchanger 2 and, after heating, are fed through pipes 3 and 4 to a stirred reactor 5 which is designed to be heated by a heating system 6. The fatty acid alkyl ester is heated to its boiling temperature and dried in the reactor unless this feedstock has already been dried. A mixture of dried sodium carbonate and glycerol is fed to the reactor through a pipe 7. The $C_1$-$C_4$ alcohol formed during the reaction, which contains part of the fatty acid alkyl ester, is removed at the head of the reactor through a pipe 8 and fed to a rectification column 9. Fatty acid alkyl ester separated off at the bottom of the column is returned to the reactor 5 through a pipe 10. The rectified $C_1$-$C_4$ alcohol is removed at the head of column 9 and fed to condenser 12 through pipe 11. Part of the alcohol can be returned as reflux to the column 9 through pipe 13. The rest of the alcohol is fed through pipe 14 to a storage container 15 for further use.

Through an alternative arrangement of pipes 7, 3 and 16, the rectification column 9 can be charged with a mixture of sodium carbonate and glycerol, so that not only rectification, but also a reaction of fatty acid alkyl esters takes place in the column. Glyceride formed in this reaction is returned to the reactor 5 together with unreacted fatty acid alkyl ester.

The installation is connected by pipe 17 to vacuum pump 18 and is operated under a light vacuum so that the reaction can be carried out at a lower temperature.

On completion of the reaction, pipe 14 is switched from the storage container 15 to a storage container 19.

At elevated temperature and under a relatively high vacuum, the unreacted ester is distilled off from the reactor 5, condensed in the condenser 12 and intermediately stored in the storage container 19.

The fatty acid alkyl ester distilled off is returned to the reactor 5 through a pipe 20 for the next batch.

After distillation of the fatty acid alkyl ester, a mixture consisting essentially of triglyceride and sodium carbonate is removed from the bottom of the reactor 5 and is fed through pipe 21 to separator 22 where the mixture is separated into its constituents. The triglyceride is removed through pipe 23 and the solid separated off through pipe 24.

The principal features of the process carried out as shown in FIG. 1 are as follows:

1. A mixture of dry sodium carbonate in dry glycerol is used as the catalyst. Sodium carbonate is sufficiently soluble in the glycerol, but not in the triglyceride, so that it is filtered off for reuse from the reaction product on completion of the reaction phase. Where sodium methylate or sodium hydroxide is used in accordance with the prior art, washing is necessary for this purpose. This leads to the formation of an emulsion and the catalyst cannot be reused.

2. The reaction, itself, is preferably controlled by addition of the glycerol phase, in which the sodium carbonate catalyst is dissolved, to the fatty acid ester which is preferably already heated to the reaction temperature. The addition rate is controlled, depending on the reaction velocity, such that the solubility limit of the glycerol in the ester is not significantly exceeded. Thus, the reaction takes place substantially in a homogeneous liquid phase, and the process is not adversely affected by delays in boiling or by excessive foaming through evaporating methanol.

3. The major portion of the initial reaction is largely completed achieving an OH value of 10 or above and usually in the range of 10-40 by the time that the addition of glycerol and sodium carbonate has been completed. The residual reaction which generally requires a longer time than the initial reaction necessitates the addition of more fatty acid methyl ester to increase or to maintain the excess of fatty acid ester and to achieve substantially full conversion as represented by OH values less than 10 and preferably less than 5. The addition of this ester component at the beginning of the reaction would not accomplish this reduction or conversion of hydroxyl groups. Instead, the reaction would stagnate in an OH value range of from about 10 to 40. The reaction mixture would continue boiling even in the after-reaction phase, i.e. for constant pressure, the reaction temperature would have to be controlled in such a way that part of the methyl ester always evaporates and is returned as reflux to the reactor, traces of reaction methanol being removed from the reaction mixture.

4. On completion of the residual reaction containing essentially only triglycerides and excess fatty acid alkyl ester, excess ester is distilled off under as low a pressure as possible to keep the temperature in the reactor low. Apart from the catalyst, only the crude triglyceride is then present in the reactor. The methyl ester distilled off may be returned with the next batch.

5. The sodium carbonate which precipitates with formation of the triglyceride is separated off by filtration, centrifugation or other adequate separation techniques. Filtration is preferably carried out at 40° to 800° C. The catalyst filtered off is preferably reused.

6. The crude glyceride is then worked up solely through distillation stages which have not been shown. There is generally no need for bleaching and/or washing.

A continuous embodiment of the process according to the invention is described with reference to FIG. 2.

Glycerol and sodium carbonate are introduced into mixing vessel 25 through pipes 26 and 27, respectively, in such a way that the sodium carbonate dissolves in the glycerol. The solution is heated to the reaction temperature in heat exchanger 28 and fed in the liquid phase onto the uppermost plate of reaction column 29. This solution and recycled fatty acid alkyl ester comprises a liquid phase which flows downwardly in column 29.

Fatty acid alkyl ester is fed through pipe 30 to heat exchanger 31 in which it is evaporated, superheated in relation to the reaction conditions (temperature and pressure) and fed in this form as superheated vapor to the middle part of the reaction column 29 through pipe 32 for the initial reaction and through pipe 33 for the residual reaction. As the liquid phase flows downwardly through the column, part of the alkyl ester is condensed and reacted forming glyceride and methanol as reaction products. The methanol evaporates and flows to the head of column 29 as a mixture with superheated ester feedstock. As the vapor flows to the head of the column, the methyl ester content decreases while the methanol content continues to increase.

In the rectification column 34 of the reaction column 29, the remaining alkyl ester is separated off from the vapor phase. It passes as liquid phase back to the uppermost plate of the reaction column while the reaction alcohol is condensed in condenser 35. A partial stream of the alcohol is returned to the rectification column 34 while the major part is removed from the system through pipe 36 in accordance with the mass balance of the entire reaction alcohol.

Additional fatty acid alkyl ester required for the residual reaction is fed into the reaction column through pipe 33 below the first point of introduction for the fatty acid alkyl ester. Preferably, the alkyl ester introduced in pipe 32 is separated by 2 to 5 plates in column 29.

The triglyceride formed collects in the sump of the reaction column 29 with the corresponding excess of fatty acid alkyl ester. It is circulated through a sump evaporator 37, methyl ester being evaporated in such a quantity that the hydraulic function of the lowermost reaction plate of the reaction column 29 is guaranteed. The product stream of the glyceride is separated off from the circulating stream through pipe 38. The residual alkyl ester has to be distilled off from this product stream in a following distillation stage (not shown). It may be returned to the reaction through the pipe 30 or employed for other purposes.

The pressure and temperature in the reaction column 29 are adjusted with respect to the alkyl ester to be reacted in such a way that the alkyl ester may be fed in as superheated vapor.

One particular feature of carrying out the reaction in this way is that a boiling equilibrium between vapor phase and liquid phase prevails in the lower part of the reaction column while the transfer of material between liquid phase and vapor phase is determined by absorption and desorption in the upper part of the column.

The process according to the invention is further illustrated in the following examples.

EXAMPLE 1

2,000 g first-cut ($C_6$–$C_{12}$) methyl ester are introduced into a 4-liter glass flask.

The ester was dried for 25 minutes at 150° C./300 mbar. 280 g glycerol containing 13 g dissolved sodium carbonate were continuously introduced over a period 2.5 h. The reaction product, methanol, evaporated during introduction of the glycerol at a sump temperature of 140°–155° C. and under a system pressure of 350–300 mbar. The vapor passed through an unregulated packed column with uncontrolled backflow. The vapor issuing at the head of the column was condensed.

After a reaction time of 3 h, another 200 g first-cut methyl ester were introduced into the reactor over a period of ½ h.

Over a reaction time of 2.5 h to 4.5 h at 300 mbar, the sump temperature rose with refluxing from 155° to 180° C. The sump temperature of 180° C. and the system pressure of 300 mbar were maintained until the reaction was over after a reaction time of 8 h.

A total of 276 g distillate was collected. After 8.5 h, a sump sample showed an OH value of 4.6 and an acid value of less than 0.1. The color values of the sump were 6.0 yellow and 1.3 red.

The sump was then filtered through PRIMISIL ® (filtration aid) to separate off the precipitated catalyst.

500 g first-cut methyl ester were distilled off first from the retort at a temperature of 145° to 205° C. and under a pressure of 150 to 60 mbar. 48.3 g dark-yellow colored head fraction were then distilled off at 170° to 247° C. under a pressure of 24 to 1 mbar.

The triglycerides were distilled over at 250° C. under a pressure of 1 mbar. A product containing 91.2% triglycerides having a color value of 3 yellow and 0.5 red distilled over whereof 85.5% had a color value of 2 yellow and 0.5 red.

Towards the end of distillation, the distillate darkened again with 16.5 g dark-brown residue remaining in the sump.

EXAMPLE 2

70 kg first-cut methyl ester were introduced into a nitrogenpurged 100-liter reactor and heated to 150° C. under a vacuum of 300 mbar.

460 g soda powder were then dissolved in 9.3 kg glycerol. The glycerol/catalyst mixture was introduced into the boiling organic phase over a period of 4 h.

From the beginning of the glycerol addition, the components reacted with one another and a methanol/ester mixture evaporated. The vapor was rectified. The reaction product, methanol, was removed from the system as head condensate. After addition of the glycerol, another 7 kg first-cut methyl ester were introduced into the boiling reaction mixture over a period of 1.5 h.

To keep the sump mixture boiling under reflux, the sump temperature was increased to 180° C. The pressure remained at 300 mbar. After a reaction time of 11.25 h, the sump sample showed an OH value of 5.1.

The entire methanol condensate was then removed from the condensate receiver.

To remove the unreacted ester, the ester was distilled off, bypassing the column, at sump temperatures of up to 183° C. and under a vacuum falling to 1.5 mbar, condensed and separately collected. After distillation of the residual ester, the sump sample showed an OH value of 3.0.

We claim:

1. A process for the production of triglycerides of fatty acids which comprises:

a) initially reacting a mixture of alkali metal carbonate catalyst and glycerol with a substantial molar excess of a $C_1$–$C_4$ alkyl ester of $C_6$–$C_{22}$ fatty acid at a temperature between about 150° C. and 250° C. at less than atmospheric pressure and under substantially anhydrous conditions to produce an initial reaction mixture containing the corresponding triglycerides of said fatty acids, and partially reacted glycerol with unreacted hydroxyl groups, b) thereafter, reacting at least a portion of said initial reaction mixture with additional $C_1$–$C_4$ alkyl ester of $C_6$–$C_{22}$ fatty acid under conditions to achieve substantially full conversion of said unreacted hydroxyl groups, and c) separating a product containing the corresponding triglycerides of said fatty acids from unreacted alkyl ester and from said alkali metal carbonate catalyst.

2. The process of claim 1 in which the molar ratio of glycerol to said alkyl ester is between about 0.15:1 and about 0.30:1.

3. The process of claim 1 in which said alkali metal carbonate comprises sodium carbonate.

4. The process of claim 1 in which said alkyl ester is a methyl ester.

5. The process of claim 1 in which said alkyl ester comprises a $C_1$-$C_4$ alkyl ester of $C_6$-$C_{12}$ fatty acids.

6. The process of claim 1 in which said alkyl ester comprises a methyl ester of $C_6$-$C_{12}$ fatty acids.

7. The process of claim 1 in which said initial reaction from step "a" is admixed with at least 10% additional alkyl ester based on the said alkyl ester employed in step "a".

8. The process of claim 11 in which conditions are maintained such that the $C_1$-$C_4$ alcohols formed in said reaction are continuously distilled from said reaction mixture together with excess alkyl ester.

9. The process of claim 8 in which distilled material is rectified and at least a portion of the alkyl ester is recycled to step a or step b.

10. The process of claim 1 in which said initial reaction of step a is carried out to achieve hydroxyl conversion represented by an OH value between about 10-40.

11. The process of claim 1 in which said reaction of step b is carried out to achieve hydroxyl conversion represented by an OH value less than about 10.

12. The process of claim 1 in which said initial reaction of step a is carried out to achieve hydroxyl conversion represented by an OH value less than about 5.

13. The process of claim 1 in which said substantially anhydrous conditions include a water content less than about 1% in said reaction mixture.

14. The process of claim in which said substantially anhydrous conditions include a water content less than about 0.1% in said reaction mixture.

15. The process of claim in which said alkali metal carbonate catalyst and glycerol are dried prior to admixing with said alkyl ester.

16. The process of claim 1 in which said alkali metal carbonate catalyst is dissolved in said glycerol prior to admixture with said alkyl ester.

17. The process of claim 1 in which said glycerol is admixed with said alkyl ester at a rate controlled such that the glycerol remains substantially soluble in said initial reaction mixture and the said step "b" reaction with additional alkyl ester is initiated after addition of all of said glycerol in step a.

18. The process of claim 1 in which unreacted alkyl ester is first separated from said triglyceride and said alkali metal carbonate catalyst is separated from the remaining triglyceride by filtration or centrifugation.

19. A process for the production of triglycerides of fatty acids which comprises:

a) adding a mixture of dry sodium carbonate and glycerol to a dried $C_1$-$C_4$ alkyl ester of $C_6$-$C_{22}$ fatty acid which is heated to a temperature of between about 150° C. to about 250° C. in a quantity corresponding to a molar ratio of glycerol to fatty acid alkyl ester of between about 0.15:1 to about 0.30:1 and at a rate such that the glycerol remains substantially soluble in the resulting reaction mixture, b) after addition of the glycerol, adding more of said alkyl ester to the reaction mixture which is maintained under boiling conditions in a quantity of at least 10%, based on the fatty acid alkyl ester used in step a), to react the unreacted hydroxyl groups of the glycerol, c) maintaining the reaction under a light vacuum and continuously distilling off $C_1$-$C_4$ alcohol which is formed, d) producing a reaction mixture which consists predominantly of fatty acid triglyceride, excess fatty acid alkyl ester and sodium carbonate, and distilling off said excess alkyl ester, e) separating said sodium carbonate from said triglyceride, and f) further purifying said triglyceride.

20. The process of claim 1 in which said fatty acid alkyl ester is methyl.

21. The process of claim 19 in which:

said mixture of sodium carbonate and glycerol is fed into the upper part of a multi-plate reaction column at an elevated temperature; said fatty acid alkyl ester is fed into a mid portion of said reaction column at a point below said mixture in the form of superheated vapor and reacts with said glycerol resulting in a downflowing mixture of triglyceride, catalyst and unreacted glycerol; additional fatty acid alkyl ester in the form of superheated vapor is fed into said reaction column at a point below said mid portion to react unreacted glycerol in said downflowing mixture; $C_1$-$C_4$ alcohol and fatty acid alkyl ester are rectified in a rectification column in communication with said reaction column and the $C_1$-$C_4$ alcohol is removed overhead, and triglyceride/fatty acid alkyl ester/sodium carbonate mixture is removed from the sump of said reaction column; fatty acid alkyl ester is evaporated in a sump evaporator and returned at least partly to the column as vapor phase above the sump and fatty acid triglyceride obtained is separated from sodium carbonate.

* * * * *